(12) United States Patent
Mori et al.

(10) Patent No.: US 10,234,062 B2
(45) Date of Patent: Mar. 19, 2019

(54) FLEXIBLE TUBE AND INSERTION APPARATUS

(71) Applicant: OLYMPUS CORPORATION, Hachioji-shi, Tokyo (JP)

(72) Inventors: Kento Mori, Hachioji (JP); Takahiro Kishi, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/606,923

(22) Filed: May 26, 2017

(65) Prior Publication Data
US 2017/0261135 A1 Sep. 14, 2017

Related U.S. Application Data

(63) Continuation of application No. PCT/JP2015/083802, filed on Dec. 1, 2015.

(30) Foreign Application Priority Data

Dec. 2, 2014 (JP) .................... 2014-244361

(51) Int. Cl.
*A61B 1/00* (2006.01)
*F16L 11/08* (2006.01)
(Continued)

(52) U.S. Cl.
CPC .......... *F16L 11/083* (2013.01); *A61B 1/0055* (2013.01); *A61B 1/00078* (2013.01);
(Continued)

(58) Field of Classification Search
CPC ............ A61B 1/00119; A61B 1/00128; A61B 1/00121; A61B 1/005; A61B 1/0055;
(Continued)

(56) References Cited

U.S. PATENT DOCUMENTS 880,882 A * 3/1908 Harris .................... F16L 11/16
138/129
916,742 A * 3/1909 Lutz ....................... F16L 11/16
138/134
(Continued)

FOREIGN PATENT DOCUMENTS

JP     S59-11827 A     1/1984
JP     S63-270021 A     11/1988
(Continued)

OTHER PUBLICATIONS

Feb. 16, 2016 Search Report issued in International Patent Application No. PCT/JP2015/083802.
(Continued)

*Primary Examiner* — Ryan Henderson
*Assistant Examiner* — Pamela F Wu
(74) *Attorney, Agent, or Firm* — Oliff PLC

(57) ABSTRACT

A flexible tube used as a part of an insertion section which defines a central axis of an insertion apparatus to be inserted into a hole, the flexible tube includes: a helical tube comprising a closely-wound region including a concave-convex portion which is provided on each of a pair of edges of a strip-shaped member elongated along a longitudinal axis, and which alternately includes convex portions and concave portions on the concave-convex portion, wherein, in a state where the strip-shaped member is spirally wound, the convex portions of the concave-convex portions facing each other along the central axis are compressed to each other; and a cylindrical outer tube which covers an outer surface of the helical tube.

14 Claims, 10 Drawing Sheets

(51) Int. Cl.
*A61B 1/005* (2006.01)
*A61M 25/00* (2006.01)
*G02B 23/24* (2006.01)

(52) U.S. Cl.
CPC ...... *A61B 1/00119* (2013.01); *A61B 1/00128* (2013.01); *G02B 23/243* (2013.01); *G02B 23/2476* (2013.01); *A61B 1/00121* (2013.01); *A61M 25/0032* (2013.01); *F16L 11/08* (2013.01); *G02B 23/2423* (2013.01)

(58) Field of Classification Search
CPC ......... A61B 1/0056; A61B 2017/00305; F16L 11/083; F16L 11/08; F16L 11/16; F16L 11/24; G02B 23/243; G02B 23/2423; A61M 25/0032; A61M 25/0012–25/0013; A61M 25/005; A61M 25/0051–25/0053
USPC ....................................................... 600/139
See application file for complete search history.

(56) References Cited

U.S. PATENT DOCUMENTS

| | | | |
|---|---|---|---|
| 4,805,595 A * | 2/1989 | Kanbara | A61B 1/00071 600/140 |
| 2006/0111617 A1 * | 5/2006 | Wimmer | A61B 1/0055 600/146 |
| 2010/0331618 A1 | 12/2010 | Galperin | |
| 2014/0155697 A1 | 6/2014 | Iede | |

FOREIGN PATENT DOCUMENTS

| | | |
|---|---|---|
| JP | H03-80701 U | 8/1991 |
| JP | H07-8443 A | 1/1995 |
| JP | 2013-097327 A | 5/2013 |
| JP | 2013-141521 A | 7/2013 |
| JP | 2014-113320 A | 6/2014 |

OTHER PUBLICATIONS

Jul. 19, 2016 Office Action issued in Japanese Patent Application No. 2016-522084.

Jun. 15, 2017 Translation of International Preliminary Report on Patentablity issued in International Application No. PCT/JP2015/083802.

* cited by examiner

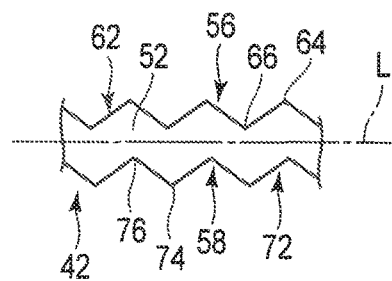
F I G. 9A
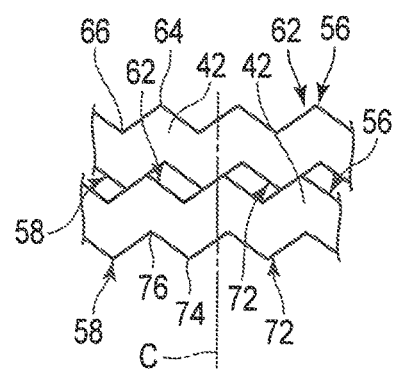
F I G. 9B
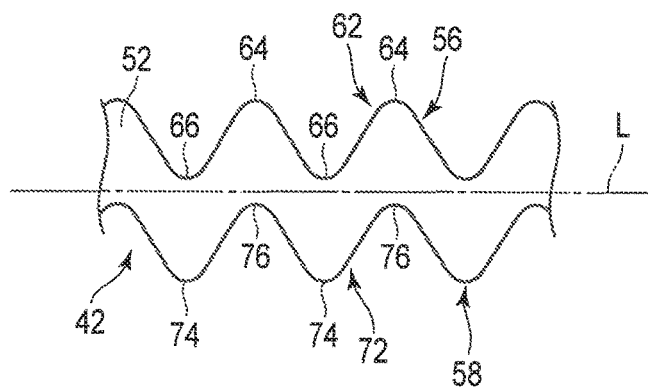
F I G. 10A

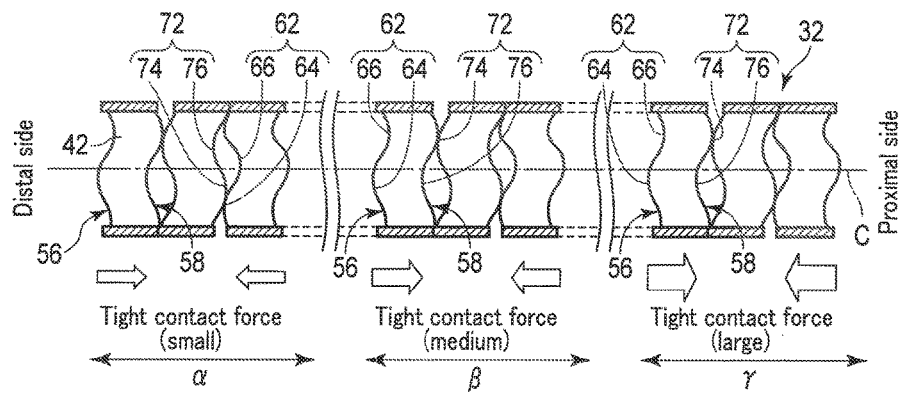
F I G. 11
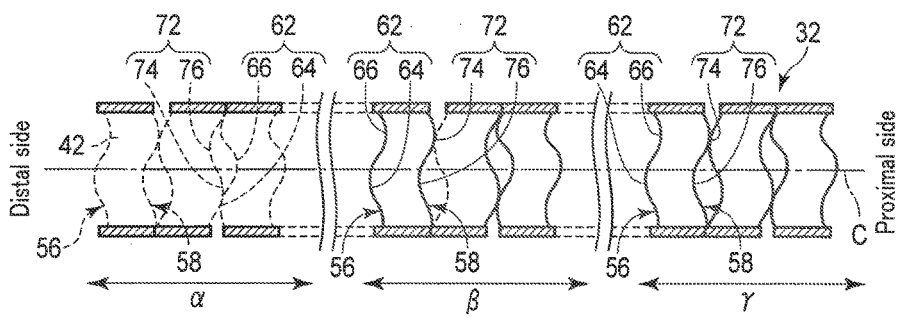
F I G. 12
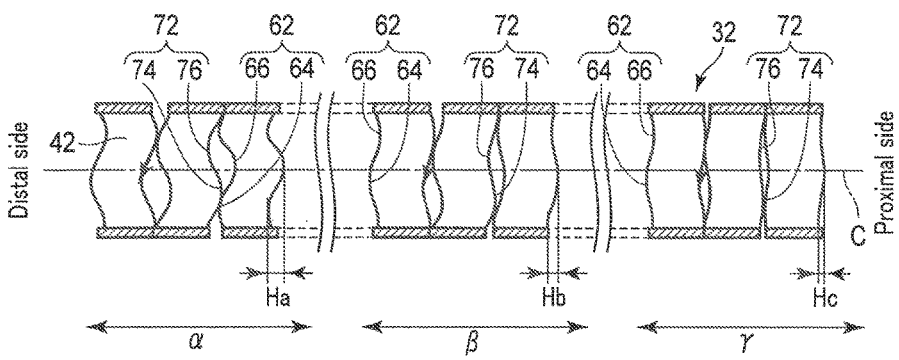
F I G. 13

FLEXIBLE TUBE AND INSERTION APPARATUS

CROSS-REFERENCE TO RELATED APPLICATIONS

This application is a Continuation Application of PCT Application No. PCT/JP2015/083802, filed Dec. 1, 2015 and based upon and claiming the benefit of priority from prior Japanese Patent Application No. 2014-244361, filed Dec. 2, 2014, the entire contents of all of which are incorporated herein by reference.

BACKGROUND OF THE INVENTION

1. Field of the Invention

The present invention relates to a flexible tube to be inserted into a hole and an insertion apparatus including the flexible tube.

2. Description of the Related Art

An endoscope disclosed in, for example, Jpn. Pat. Appln. KOKAI Publication No. 2013-97327 discloses a flexible tube for an endoscope which includes a helical tube alternately including a closely-wound region and a sparsely-wound region along a central axis. The flexible tube has adequate resiliency (ease of returning from a bent state), and can be bent smoothly when external force is applied. Therefore, for an endoscope having such a flexible tube, insertability of an insertion section is intended to be improved with respect to a hole.

BRIEF SUMMARY OF THE INVENTION

According to one aspect of the present invention, a flexible tube used as a part of an insertion section which defines a central axis of an insertion apparatus to be inserted into a hole, includes: a helical tube comprising a closely-wound region including a concave-convex portion which is provided on each of a pair of edges of a strip-shaped member elongated along a longitudinal axis, and which alternately includes convex portions and concave portions on the concave-convex portion, wherein, in a state where the strip-shaped member is spirally wound, the convex portions of the concave-convex portions facing each other along the central axis are compressed to each other; and a cylindrical outer tube which covers an outer surface of the helical tube.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 9A is a schematic view of a part of a strip-shaped member configuring a helical tube of a flexible tube of an insertion section of an insertion apparatus according to a first modification of the first embodiment.

FIG. 9B is a schematic view of a part of the helical tube, in which, while the strip-shaped member shown in FIG. 9A is wound and molded spirally, an edge on one side and an edge of the other side on the strip-shaped member adjacent to each other along a central axis have a part that abut each other in a substantially linear state by a tight contact force caused by an initial tension.

FIG. 10A is a schematic view of a part of a strip-shaped member configuring a helical tube of a flexible tube of an insertion section of an insertion apparatus according to a second modification of the first embodiment.

FIG. 11 is a schematic view of a helical tube, in which a first region, a second region, and a third region arranged in this order from a distal side to a proximal side of the helical tube of a flexible tube of an insertion section of an insertion apparatus according to a second embodiment are shown, and an edge on one side and an edge on the other side of a strip-shaped member adjacent to each other along a central axis are made constant in each region and abut each other in a state where a part thereof is abutted by a tight contact force caused by an initial tension that gradually increases in the order of the first region, the second region, and the third region.

FIG. 12 is a schematic view of a helical tube, in which a first region, a second region, and a third region of the helical tube of a flexible tube of an insertion section of an insertion apparatus according to a third embodiment are shown, and a part thereof is in an abutted state by a tight contact force caused by an initial tension, in a state where an edge on one side and an edge on the other side of a strip-shaped member adjacent along a central axis in the first region are processed to reduce a friction coefficient so as to allow easy slidability with respect to each other, an edge on one side is processed to reduce the friction coefficient and an edge on the other side is not processed in the second region, and both of an edge on one side and an edge of the other side are not processed in the third region.

FIG. 13 is a schematic longitudinal sectional view of a first region, a second region, and a third region of a helical tube of a flexible tube of an insertion section of an insertion apparatus according to a fourth embodiment, showing a state in which a difference between an apex of a convex portion and a most concaved position of a concave portion of a concave-convex portion of an edge on one side, and a difference between an apex of a convex portion and a most concaved position of a concave portion of a concave-convex portion of an edge on the other side of a strip-shaped member adjacent along a central axis are changed in each region.

DETAILED DESCRIPTION OF THE INVENTION

Hereinafter, embodiments of the present invention will be explained with reference to the drawings.

[First Embodiment]

The first embodiment will be explained with reference to FIG. 1 to FIG. 8.

Figure 1:
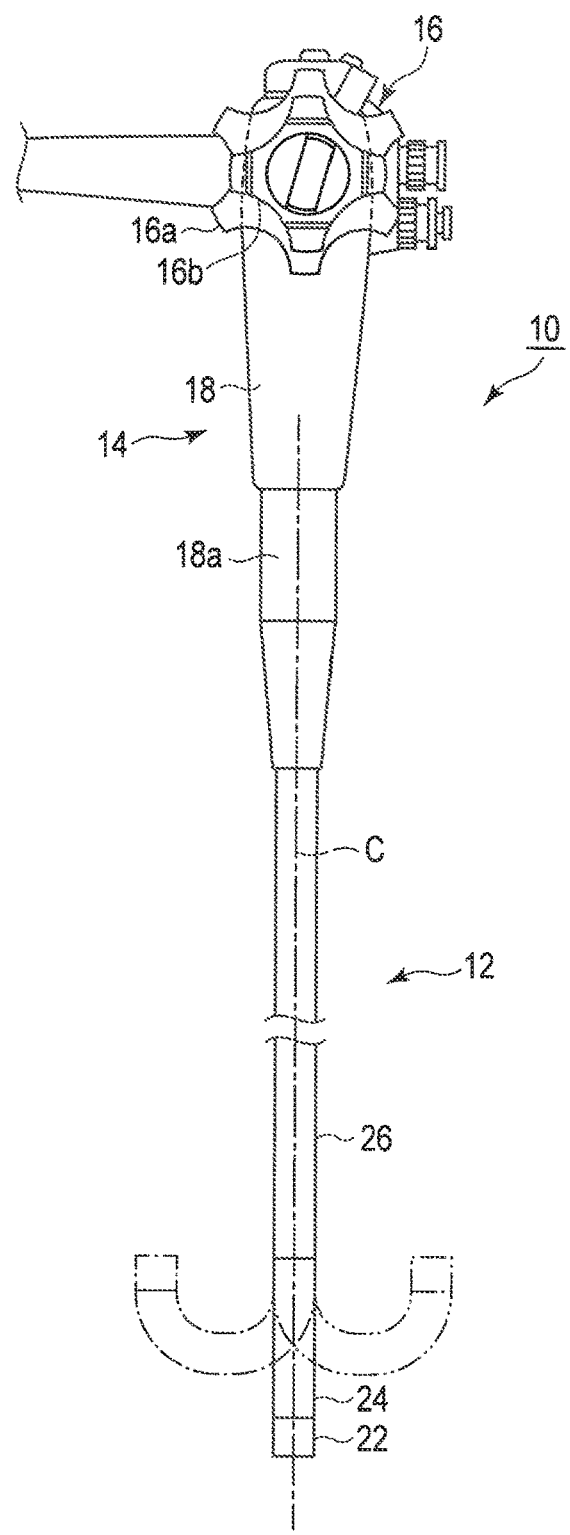
FIG. 1 is a schematic view of an endoscope as an insertion apparatus according to a first embodiment to a fifth embodiment.

As shown in FIG. 1, an insertion apparatus 10 such as an endoscope includes an elongated insertion section 12 which is able to be inserted into, for example, a hole such as a body cavity. The insertion section 12 defines a central axis C by its distal end and proximal end. In the present embodiment, the insertion apparatus 10 includes an operation section 14 at the proximal end of the insertion section 12, which is gripped by a user to perform various types of operations. The operation section 14 includes an operation section main body 16 on which a UD knob 16a and a RL knob 16b are arranged, and a grip section 18 which is gripped by the user and arranged at the proximal end (a proximal end of a flexible tube 26 explained later on) of the insertion section 12 through a protection hood 18a.

The insertion section 12 includes a distal rigid portion 22, a bending portion 24, and a flexible tube 26 from the distal end toward the proximal end thereof along the central axis C. The distal rigid portion 22 is located at the furthest end of the insertion section 12, on which, for example, an end of an illumination optical system, an end of an observation optical system, and an end of a channel (all of which are not shown) are disposed. The bending portion 24 is bendable upwards and downwards by the operation of the UD knob 16a of the operation section 14. The bending portion 24 is also bendable rightwards and leftwards by the operation of the RL knob 16b of the operation section 14.

Figure 2:
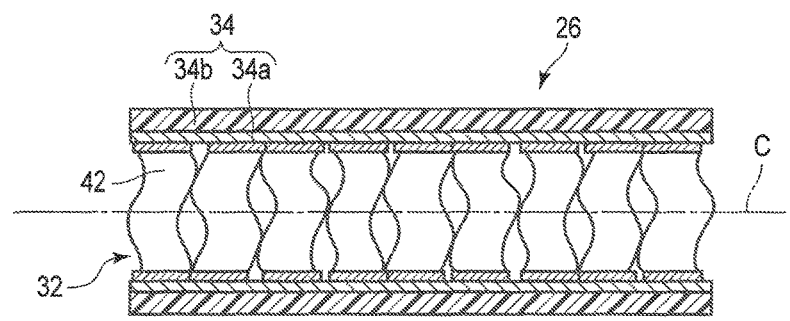
FIG. 2 is a schematic longitudinal sectional view of a part of a flexible tube of an insertion section of the insertion apparatus according to the first embodiment.

As shown in FIG. 2, the flexible tube (coiled hose part) 26 has a hollow shape. The flexible tube 26 includes a helical tube (flex) 32 and a cylindrical outer tube 34 that is arranged on the outer side of the helical tube 32 and covers an outer surface of the helical tube 32. The flexible tube 26 is formed the longest in the insertion section 12.

Here, as shown in FIG. 2, the outer tube 34 is formed by a net-like tube (braid) 34a disposed on the outer side of the helical tube 32 in cooperation with a resin material layer 34b disposed on the outer side of the net-like tube 34a. In other words, the flexible tube 26 has a three-layer structure including the helical tube 32, the net-like tube 34a, and the resin material layer 34b. The net-like tube 34a is formed of a fine thread made of metallic material or by braiding a fine thread which is a combination of a metallic material and a resin material. The resin material layer 34b is formed by, for example, extrusion molding. The net-like tube 34a and the resin material layer 34b of the outer tube 34 are integrally molded. For the resin material layer 34b of the outer tube 34, a fabric that cannot easily change in length and cannot easily expand or contract radially is selected and used. For the resin material layer 34b of the outer tube 34, a fabric that can endure washing and disinfection/sterilization is selected as appropriate and used. Furthermore, to simplify the explanation, here, the outer tube 34 is considered as being uniform without a change in the difficulty of bending from its distal end to its proximal end.

Figure 3:
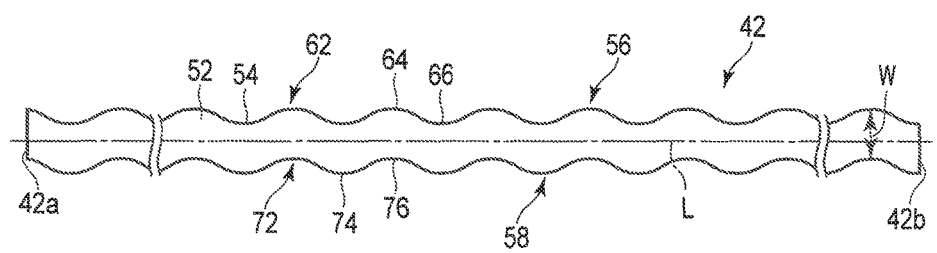
FIG. 3 is a schematic view of a strip-shaped member that configures a helical tube of the flexible tube of the insertion section of the insertion apparatus according to the first embodiment.
Figure 4:
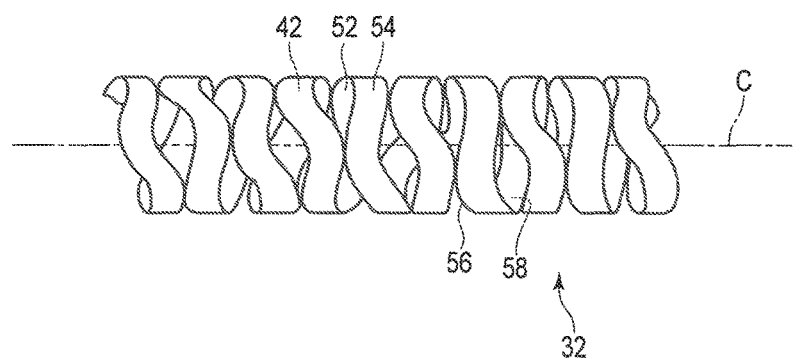
FIG. 4 is schematic view of the helical tube used for the flexible tube of the insertion section of the insertion apparatus according to the first embodiment, in which, while the strip-shaped member shown in FIG. 3 is wound and molded spirally, an edge on one side and an edge on the other side of the strip-shaped member adjacent to each other along a central axis have a part that abut each other in a substantially point-like state by a tight contact force caused by an initial tension.

The helical tube 32 is formed in a state shown in FIG. 4, where a strip-shaped member 42 shown in FIG. 3 is wound spirally. The strip-shaped member 42 is formed by pressing, plastic working, and cutting, etc. a metal material such as stainless steel and bronze. The length of the strip-shaped member 42 itself shown in FIG. 3, which is elongated along a longitudinal axis L, is formed sufficiently longer than a width W perpendicular to the longitudinal axis L of the strip-shaped member 42. The width W of the strip-shaped member 42 is formed larger than the thickness of edges 56 and 58 of the strip-shaped member 42 (thickness of the strip-shaped member 42). The strip-shaped member 42 according to the present embodiment is preferred to have, for example, a constant thickness.

The helical tube 32 obtained by winding the strip-shaped member 42 spirally shown in FIG. 4 is formed as an elastic tube with an appropriate elastic force (resiliency) that allows bending from a straight state by adding an external force that includes gravity. The strip-shaped member 42 shown in FIG. 3 and FIG. 4 includes a portion 52 that is to be an inner circumference surface facing the inner side and a portion 54 that is to be an outer circumference surface facing the outer side of the helical tube 32 in a wound state, and a pair of edges 56 and 58.

As shown in FIG. 3, on the edge 56 on one side of the strip-shaped member 42, a first concave-convex portion 62 is formed along the longitudinal axis L of the strip-shaped member 42. The first concave-convex portion 62 alternately includes convex portions (peak parts) 64 and concave portions (valley parts) 66. On the edge 58 on the other side of the strip-shaped member 42, a second concave-convex portion 72 is formed along the longitudinal axis L of the strip-shaped member 42. The second concave-convex portion 72 alternately includes convex portions (peak parts) 74 and concave portions (valley parts) 76. It is preferred that the first and second concave-convex portions 62 and 72 be formed continuously from one end (distal end) 42a to the other end (proximal end) 42b along the longitudinal axis L of the strip-shaped member 42. In other words, it is preferred that the first and second concave-convex portions 62 and 72 are formed across the entire length of the strip-shaped member 42. Here, the first and second concave-convex portions 62 and 72 of the strip-shaped member 42 are formed respectively in a wave-like shape with a continuous sine wave. The width W of the strip-shaped member 42 is approximately constant. In the width W direction perpendicular to the longitudinal axis L of the strip-shaped member 42, the opposite side of the peak part of the convex portion 64 of the first concave-convex portion 62 of the edge 56 on one side in the width direction (a portion protruding the most on the outer side in the width W direction), corresponds to the most concaved portion or the vicinity thereof of the concave portion 76 of the second concave-convex portion 72 of the edge 58 on the other side. The same also applies to the concave portion 66 and the convex portion 74. Therefore, it is preferred that the first and second concave-convex portions 62 and 72 are respectively formed in approximately the same size and approximately the same shape.

Figure 5:
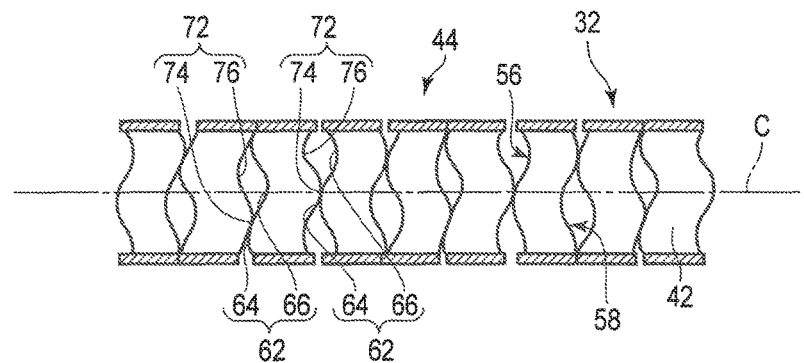
FIG. 5 is a schematic longitudinal sectional view of a part of the helical tube of the flexible tube of the insertion section of the insertion apparatus according to the first embodiment.

As shown in FIG. 4 and FIG. 5, in the helical tube 32, the convex portion 64 formed on the edge 56 on one side of the strip-shaped member 42 and the convex portion 74 formed on the edge 58 on the other side adjacent along the central axis C of the flexible tube 26, that is, the convex portions 64 and 74, are in tight contact in a manner compressing each other along the axial direction of the central axis C by being applied an initial tension. Here, it is preferred that the convex portion 64 formed on the edge 56 on one side and the convex portion 74 formed on the edge 58 on the other side adjacent along the central axis C of the flexible tube 26 are in tight contact across the entire length from the distal end to the proximal end of the helical tube 32 in a manner compressing each other along the axial direction of the central axis C by being applied the initial tension. In other words, in the present embodiment, the helical tube 32, from its distal end to the proximal end, is formed as a closely-wound region 44 in which the concave-convex portions 62 and 72 adjacent along the central axis C attempt to come in tight contact with each other. Since the helical tube 32 is formed as the closely-wound region 44 across the entire length in the above manner, even if the outer tube 34 does not exist, this helical tube 32 easily maintains a straight shape when the central axis C is turned horizontally, and undergoes less change in the entire length when the central axis C is placed vertically. To simplify the explanation, in the present embodiment, the tight contact force in which the concave-convex portions 62 and 72 adjacent along the central axis C attempt to come in tight contact with each other is considered as being constant. The concave-convex portions 62 and 72 adjacent along the central axis C come in contact with each other in an approximately point-like manner and the tight contact force is applied in an approximately point-like manner. On the other hand, portions other than where the tight contact force is applied among the concave-convex portions 62 and 72 have a gap formed between the adjacent edges 56 and 58 (concave portions 66 and 76).

The resiliency of the flexible tube 26 is decided depending on an insertion target. Therefore, depending on the insertion target, it is preferred that a sparsely-wound region in which a tight contact force is not applied to the concave-convex portions 62 and 72 adjacent along the central axis C is formed on, for example, a part of the distal end and the proximal end among the parts of the helical tube 32.

Here, as shown in FIG. 4 to FIG. 7B, regardless of whether the helical tube 32 is in a straight state or in a bent state, a position off the apex of the convex portion 64 of the edge 56 of one side of the strip-shaped member 42 contacts a position off the apex of the convex portion 74 of the edge 58 of the other side in a tightly contacted manner. The concave-convex portions 62 and 72 adjacent along the central axis C of the helical tube 32 are in contact with each other at a position off the peaks of the convex portions 64 and 74. As shown in FIG. 4 and FIG. 5, in a state where the helical tube 32 is straight, the concave portion 66 adjacent to the convex portion 64 of the edge 56 on one side along the longitudinal axis L, and the concave portion 76 adjacent to the convex portion 74 of the edge 58 on the other side along the longitudinal axis L, face each other forming a space between each other.

An outer tube 34, which forms the outer circumference surface of the flexible tube 26, covers the outer side of the helical tube 32 formed in the above manner. The helical tube 32 and the outer tube 34 (for example, the net-like tube 34a of the outer tube 34) are fixed at the distal end part and the proximal end part of the flexible tube 26 by, for example, soldering, bonding, or laser welding.

Even if the outer tube 34 is linear or bent, the length along the central axis C does not change. Therefore, similar to the outer tube 34, even if the helical tube 32 fixed on the inner side of the outer tube 34 is linear or bent, the length along the central axis C does not change.

As shown in FIG. 1, on the distal side of the flexible tube 26 is disposed a bending portion 24, on the distal end of which a distal rigid portion 22 is fixed. An operation section 14 is disposed on the proximal side of the flexible tube 26. In the above manner, the insertion apparatus 10 is formed.

The mechanism of the insertion apparatus (for example, an endoscope) 10 according to the present embodiment will be explained in the following.

First, primarily the movement of the helical tube 32 in the case of changing the state of the flexible tube 26 from a straight state to a bent state will be explained.

Figure 6:
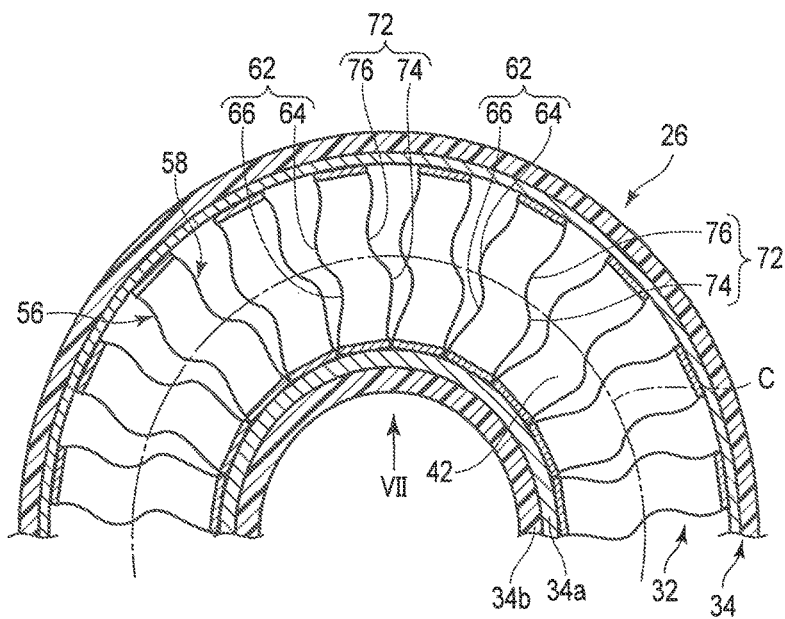
FIG. 6 is a schematic longitudinal sectional view of a state in which a part of the flexible tube of the insertion section of the insertion apparatus is bent according to the first embodiment.

The flexible tube 26 is bent from a linear state shown in FIG. 2 to a state shown in FIG. 6 by applying an external force from a direction deviated from the central axis C, such as a direction perpendicular to the central axis C. Even in this case, the length of the outer tube 34 along the central axis C does not change. In the outer tube 34, a portion on the inner side of a bending radius that coincides with the central axis C is compressed and shrinks, and a portion on the outer side extends.

In the case of bending the flexible tube 26, in the helical tube 32 arranged on the inner side of the outer tube 34, a large compressing force is added to the compressing force (tight contact force) of that in a straight state between the edge 56 on one side and the edge 58 on the other side of a portion to be the inner side of the bending radius that coincides with the central axis C among the portions of the strip-shaped member 42 that are adjacent along the central axis C. As shown in FIG. 6, in the helical tube 32, the edge 56 on one side and the edge 58 on the other side of a portion to be the outer side of the bending radius that coincides with the central axis C among the portions of the strip-shaped member 42 that are adjacent along the central axis C become separated from each other.

Figure 7A:
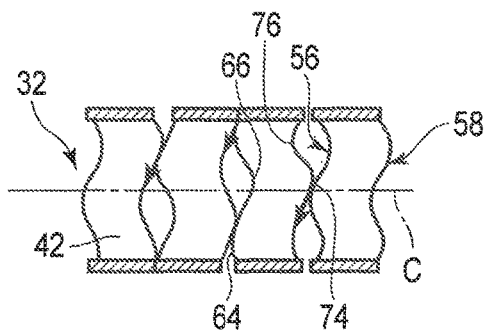
FIG. 7A is a schematic longitudinal sectional view of a state where an attempt is made to bend the helical tube of the flexible tube from a straight state shown in FIG. 2 to a state shown in FIG. 6 when observing the flexible tube of the insertion section of the insertion apparatus from a direction indicated by arrow VII in FIG. 6 according to the first embodiment.
Figure 7B:
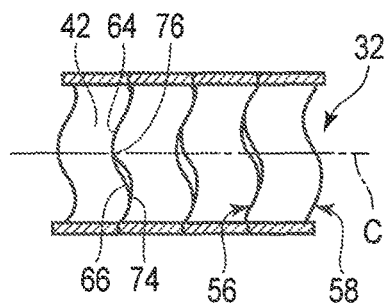
FIG. 7B is a schematic longitudinal sectional view of a part of the helical tube of the flexible tube when observing, from the direction indicated by the arrow VII in FIG. 6, the helical tube in a state where the flexible tube of the insertion section of the insertion apparatus is bent according to the first embodiment.

As shown in FIG. 7, before bending the flexible tube 26, at the portion to be the inner side of the bending radius in the helical tube 32, the strip-shaped member 42 is such that the convex portion 64 of the edge 56 on one side comes in contact at a position off the apex in the vicinity of the apex of the convex portion 74 of the edge 58 on the other side that is adjacent along the central axis C. When the flexible tube 26 is bent, a compressing force is applied to a portion that becomes the inner side of the bending radius in the helical tube 32. Therefore, in the strip-shaped member 42, the convex portion 64 of the edge 56 on one side moves from the vicinity of the apex of the convex portion 74 of the edge 58 on the other side that is adjacent along the central axis C while sliding towards the concave portion 76 that is adjacent along the longitudinal axis L. At this time, until the convex portion 64 of the edge 56 on one side comes close to the concave portion 76 from the vicinity of the apex of the convex portion 74 of the edge 58 on the other side adjacent along the central axis C, the convex portion 64 consistently maintains a state in which it is in contact with the convex portion 74 and/or the concave portion 76. Therefore, the convex portion 64 of the edge 56 on one side moves from a position (see FIG. 7A) adjacent to the apex of the convex portion 74 of the edge 58 on the other side to a position shown in FIG. 7B while sliding towards the concave portion 76 of the edge 58 on the other side.

In the above manner, at a portion that becomes the inner side of the bending radius in the helical tube 32 before and after bending the flexible tube 26, the concave-convex portion 62 of the edge 56 on one side and the concave-convex portion 72 of the edge 58 on the other side of the strip-shaped member 42 adjacent along the central axis C of the helical tube 32 are maintained in a tightly contacted state by the compressing force.

As mentioned above, when bending the flexible tube 26, at a portion that becomes the outer side of the bending radius in the flexible tube 26, the convex portion 64 of the edge 56 on one side of the strip-shaped member 42 is separated in parallel to the central axis C from the vicinity of the apex of the convex portion 74 of the edge 58 on the other side adjacent along the central axis C.

Therefore, at a portion that becomes the inner side of the bending radius in the helical tube 32, the edges 56 and 58 (concave-convex portions 62 and 72) adjacent along the axial direction of the central axis C become closer to each other, reducing the gap, in an appropriate range. At a portion that becomes the outer side of the bending radius, the strip-shaped member 42 adjacent along the axial direction of the central axis C become separated from each other in an appropriate range. Therefore, the helical tube 32, while maintaining the length of the central axis C thereof, is bent by moving the strip-shaped member 42 of the helical tube 32.

In this manner, the flexible tube 26 is bent by making the helical tube 32 and the outer tube 34 function appropriately. Furthermore, when bending the flexible tube 26 by applying an external force, a portion that becomes the inner side of the bending radius of the helical tube 32 shrinks, and, similar to the outer tube 34, the length along the central axis C does not change. Therefore, the flexible tube 26 can be bent smoothly without interference by the outer tube 34 and the helical tube 32.

In the helical tube 32 of the present embodiment, the first concave-convex portion 62 is formed continuously on the edge 56 on one side, and the second concave-convex portion 72 is formed continuously on the edge 58 on the other side, from one end (distal end) 42a to the other end (proximal end) 42b of the strip-shaped member 42. The helical tube 32 according to the present embodiment is formed uniformly from the distal end to the proximal end thereof along the central axis C. Therefore, the flexible tube 26 including the helical tube 32 according to the present embodiment has a constant unbendability (hardness) regardless of the position from the distal end to the proximal end thereof.

Therefore, the flexible tube 26 according to the present embodiment does not have a portion at which the hardness against bending (unbendability) changes drastically. Furthermore, in the helical tube 32 of the flexible tube 26, the adjacent first and second concave-convex portions 62 and 72 consistently contact each other by the initial tension. Therefore, the portion to become the outer side of the bending radius tries to maintain a state in which the concave-convex portions 62 and 72 contact each other against a force acting to separate the concave-convex portions 62 and 72. Therefore, the flexible tube 26 according to the present embodiment exercises constant resistance to bending. As explained above, in comparison to a flexible tube including a helical tube that has a sparsely-wound region in which the initial tension is not applied entirely on an edge on one side and an edge on the other side of a strip-shaped member, the flexible tube 26 including the helical tube 32 according to the present embodiment has a constant unbendability at any position.

In the following, the movement of the helical tube 32 when returning the flexible tube 26 to a straight state from a bent state, i.e., resiliency, will be explained.

As mentioned above, the helical tube 32 according to the present embodiment is formed uniformly from the distal end to the proximal end thereof along the central axis C. Therefore, the flexible tube 26 including the helical tube 32 according to the present embodiment not only has a constant unbendability (hardness) but also has a constant resiliency (returnability) regardless of the position from the distal end to the proximal end thereof. Furthermore, this flexible tube 26 does not have a portion at which the returnability from a bent state to a substantially linear state changes drastically.

By the initial tension being applied, the helical tube 32 is formed so that the edge 56 on one side and the edge 58 on the other side of the strip-shaped member 42 adjacent to each other along the central axis C are in tight contact with each other. Therefore, when the external force is removed from the flexible tube 26, the edge 56 on one side and the edge 58 on the other side of a portion to become the outer side of the bending radius of the helical tube 32 become close and come in contact with each other, exercising a tight contact force with respect to each other caused by the initial tension. Here, the convex portion 64 of the edge 56 on one side maintains a state in which it is abutted in the vicinity of the apex of the convex portion 74 of the edge 58 on the other side.

At a portion to become the inner side of the bending radius of the helical tube 32, along with the edge 56 on one side and the edge 58 on the other side of the portion to be the outer side of the bending radius being drawn close to each other, the convex portion 64 of the edge 56 on one side formed on the strip-shaped member 42 moves towards the vicinity of the apex of the convex portion 74 from the position of the concave portion 76 of the edge 58 on the other side adjacent along the central axis C. Here, until the convex portion 64 of the edge 56 on one side comes close to the vicinity of the apex of the convex portion 74 from the concave portion 76 of the edge 58 on the other side, the convex portion 64 consistently maintains a state in which it is abutted to the convex portion 74 and/or the concave portion 76. In other words, the concave-convex portions 62 and 72 facing each other along the central axis C in the helical tube 32 are capable of moving with respect to each other in accordance with the bending of the flexible tube 26 while maintaining a state in which the apexes of the convex portions 64 and 74 facing each other along the central axis C and the concave portions 66 and 76 adjacent along the longitudinal axis L are in contact with each other.

In the above manner, the flexible tube 26 is returned to the straight state shown in FIG. 2 from the bent state shown in FIG. 6.

At the portion to become the outer side of the bending radius, the edge 56 on one side and the edge 58 on the other side are separated by the bending of the flexible tube 26. At the portion to become the inner side of the bending radius, the edge 56 on one side and the edge 58 on the other side are formed to be in tight contact with each other. This remains the same from the distal end to the proximal end of the helical tube 32. Since the helical tube 32 of the flexible tube 26 according to the present embodiment does not include a sparsely-wound region, the flexible tube 26 is controlled from the change in returnability for returning to a substantially straight state from a bent state. Therefore, in comparison to a flexible tube which includes a helical tube including a sparsely-wound region in which the initial tension is not applied entirely on an edge on one side and an edge on the other side of a strip-shaped member, the flexible tube 26 including the helical tube 32 according to the present embodiment exercises uniform resiliency (returnability from a bent state) at any position.

Furthermore, particularly in a case where a bending amount of the flexible tube 26 is small and a bending radius R is large, a significant influence from a tight contact force which attempts to tightly contact the concave-convex portions 62 and 72 is expressed. Therefore, in the flexible tube 26 of the present embodiment, a force to moderately return to a linear state (resiliency) from a bent state is expressed significantly than in a flexible tube including a helical tube in which gaps are formed continuously between the edges of the strip-shaped member.

Next, a mechanism of when inserting the insertion section 12 from its distal end (distal rigid portion 22) from an entrance inside a hole (here, an appropriate passage with a bent portion) towards a deeper end side using the flexible tube 26 of the insertion apparatus 10 will be explained in the following.

When inserting the insertion section 12 from its distal end into the passage, a user of the insertion apparatus 10 grips the operation section 14 by the left hand, and holds a portion of the flexible tube 26 close to its distal end by the right hand. Here, the user may operate the knobs 16a and 16b of the operation section 14 by the left hand finger to bend the bending portion 24 and direct the distal rigid portion 22 of the insertion section 12 to an appropriate direction. The insertion section 12 is inserted into an appropriately bent narrow passage, such as from the nose to the stomach, or from the anus to the large intestine in the order of the distal rigid portion 22, the bending portion 24, and the flexible tube 26. The user changes the gripping position gradually to a position on the proximal side of the flexible tube 26 to insert the distal rigid portion 22 of the insertion section 12 deeper into the passage. Here, the distal rigid portion 22 of the insertion section 12 will be explained in particular as being inserted from the anus of the large intestine to the far side (deep portion) as the passage.

As the insertion section 12 is inserted into the appropriately bent passage (for example, the intestinal canal such as the large intestine), the flexible tube 26 receives an external force (including gravity) from the inner circumference surface (inner wall) of the passage, from a direction deviated from a direction along the central axis C of the flexible tube 26 (for example, a direction perpendicular thereto). In the case where the applied external force is smaller than the unbendability of the flexible tube 26, the flexible tube 26 is maintained in a linear state without deflecting. In other words, the flexible tube 26 is able to maintain a substantially linear state and is inserted into the passage without deflecting.

In the case where the external force (including gravity) applied from the inner circumference surface of the passage is equal to or larger than the unbendability of the flexible tube 26, the flexible tube 26 will start deflecting from the substantially linear state. In other words, the flexible tube 26 will be bent from the substantially linear state.

The flexible tube 26 is formed to have a moderately large resiliency by the tight contact force exercised at appropriate intervals along the longitudinal axis L of the strip-shaped member 42 at the concave-convex portions 62 and 72 of the edges 56 and 58 of the strip-shaped member 42 of the helical tube 32. In other words, by the tight contact force between the concave-convex portions 62 and 72, this flexible tube 26 is set so that a force acting to return to a moderate linear state from a bent state becomes larger than the flexible tube in which gaps are formed continuously on the edges of the strap shaped member of the helical tube.

Here, when the distal end of the insertion section 12 is inserted to the large intestine from the anus side towards the deep portion, the insertion section 12 is inserted while shortening the intestinal canal of the large intestine using the curve of the bending portion 24 and the resiliency of the flexible tube 26, etc. For example, the bending portion 24 is bent so as to direct the distal end of the distal rigid portion 22 of the insertion section 12 to an insertion direction (deep portion) of the curved passage. When the flexible tube 26 is pushed in by the right hand while restoring the curve of the bending portion 24, the flexible tube 26 may be bent by an external force from the bent portion of the passage. Even if the flexible tube 26 is bent by the tight contact force between the concave-convex portions 62 and 72 of the helical tube 32, the resiliency acts to return the shape of the flexible tube 26 to an approximately linear state. This resiliency is approximately constant from the distal end to the proximal end of the flexible tube 26. Furthermore, particularly in a case where a bending amount of the flexible tube 26 is small (bending radius R is large), the shape of the flexible tube 26 easily returns to the approximately linear state, thereby allowing the deflected intestinal canal to be adjusted in an approximately linear state. In the above manner, when the flexible tube 26 is in a linear state, the distal end of the distal rigid portion 22 of the insertion section 12 may be moved further into the deep portion of the large intestine.

On the other hand, when inserting the distal rigid portion 22 of the insertion section 12 to a bent portion in the passage by appropriate manipulation of the right hand while holding the flexible tube 26 by the right hand, the flexible tube 26 exercises an appropriate unbendability. Therefore, the pushing force with which the flexible tube 26 is inserted into the far side inside the passage while being gripped by the right hand can be transmitted reliably.

By using the insertion section 12 including the flexible tube 26 according to the present embodiment, the operation of shortening the intestinal canal of the large intestine and pushing the insertion section 12 into the deep portion of the large intestine (passage) may be more easily performed.

In the above manner, although the flexible tube 26 of the insertion section 12 may be bent appropriately in response to the external force applied from the inner circumference surface of the passage, while being returned to the substantially linear state by the resiliency, the insertion section 12 including the flexible tube 26 mentioned above moves the distal rigid portion 22 of the insertion section 12 to the far side in the passage.

Here, the first and second concave-convex portions 62 and 72 are formed continuously from the distal end to the proximal end of the helical tube 32, and a tight contact force caused by the initial tension is applied per an appropriate interval (intervals of apexes of the convex portions 64 adjacent to each other along the longitudinal axis L). Therefore, from the distal end up to the proximal end of the flexible tube 26, the difference in resiliency and the difference in unbendability are not present or are hardly present. Even locally, the difference in resiliency and the difference in unbendability are not present or are hardly present. Therefore, the amount of operational force at the proximal end portion of the flexible tube 26 held by the right hand of the user of the insertion apparatus 10 is easily transmitted to the distal end of the flexible tube 26 from the gripping position, and the flexible tube 26 can be easily inserted into the far side in the passage.

As explained above, according to the insertion apparatus 10 related to the present embodiment, the following effects may be obtained.

The flexible tube 26 according to the present embodiment includes a uniform helical tube 32 in which the convex portion 64 of the concave-convex portion 62 of the edge 56 on one side and the convex portion 74 of the concave-convex portion 72 of the edge 58 on the other side of the adjacent strip-shaped member 42 are in tight contact with each other. In other words, the concave-convex portions 62 and 72 are formed continuously from the distal end to the proximal end of the helical tube 32. Therefore, the resiliency and unbendability of the flexible tube 26 are respectively approximately constant from one end to the other end thereof. Therefore, the returnability (resiliency) against bending and the hardness against bending (unbendablity) of the flexible tube 26 do not change significantly along the central axis C. Therefore, when inserting the insertion section 12 into a hole, such as into a body cavity, the flexible tube 26 is not easily deflected, or, even if it is deflected, can easily return to its original state (the straight state). Therefore, when inserting the distal end of the flexible tube 26, moreover, the distal end (distal rigid portion 22) of the insertion section 12 of the insertion apparatus 10 to insert the flexible tube 26 towards the far side of the passage, the operation of pulling on the passage to shorten it may be easily performed. Therefore, according to the present embodiment, the flexible tube 26 may be provided with favorable insertability.

The strip-shaped member 42 is abutted in a state where the apex of the convex portion 64 of the concave-convex portion 62 of the edge 56 on one side, and the apex of the convex portion 74 of the concave-convex portion 72 of the edge 58 on the other side adjacent along the longitudinal axis, are deviated from each other. In other words, the convex portion 64 of the concave-convex portion 62 of the edge 56 on one side comes in contact at a position moved towards the concave portion 76 from the apex of the convex portion 74 of the concave-convex portion 72 of the adjacent edge 58 on the other side so that pressure is applied to each other along the central axis C. Therefore, when the flexible tube 26 is bent, the apex of the convex portion 64 of the concave-convex portion 62 of the edge 56 on one side always moves towards a certain adjacent concave portion 76 of the concave-convex portion 72 of the edge 58 on the other side. Here, since each of the concave-convex portions 62 and 72 are formed in the shape of a sine wave, the flexible tube 26 can be bent smoothly without being stuck.

Meanwhile, also when the bent flexible tube 26 is returned to a straight state by the resiliency of the flexible tube 26, it can be returned to the straight state without being stuck.

If the apexes of the convex portions (peak parts) 64 and 74 formed on the strip-shaped member 42 are in tight contact with each other, there is a possibility that only a reactive force would occur between the apexes when attempting to bend the flexible tube, which would maintain a state where the convex portion 64 of the edge 56 on one side contacts the convex portion 74 of the edge 58 on the other side, and would not cause the convex portion 64 of the edge 56 on one side to shift towards the convex portion 74 of the edge 58 on the other side, and the convex portion 74 of the edge 58 on the other side to shift towards the concave portion 66 of the edge 56 on the one side. Therefore, when an external force is applied to the flexible tube 26, and a compressing force is applied to the strip-shaped member 42, there is a possibility that the apex of the convex portion 64 of the edge 56 on one side may not move to the concave portion 76 on either side from the apex of the convex portion 74 of the edge 58 on the other side, which would not allow the flexible tube 26 to bend smoothly.

In contrast, in the helical tube 32 of the flexible tube 26 according to the present embodiment, the convex portion 64 of the concave-convex portion 62 of the edge 56 on one side and the convex portion 74 of the concave-convex portion 72 of the edge 58 on the other side of the adjacent strip-shaped member 42 are in tight contact with each other with their apexes deviated from each other. Therefore, when an external force is applied to the flexible tube 26, and a compressing force is applied to the strip-shaped member 42, the convex portion 64 of the edge 56 on one side moves towards the concave portion 76 at a determined position without passing the apex from the convex portion 74 of the edge 58 on the other side. Therefore, the flexible tube 26 can be bent smoothly.

Furthermore, the helical tube 32 according to the present embodiment can be formed only by forming wave-like concave-convex portions 62 and 72 on the edges 56 and 58 of the strip-shaped member 42, and, while winding them spirally, applying the initial tension so as to apply the tight contact force between each of the concave-convex portions 62 and 72. Therefore, the helical tube 32 can be manufactured easily.

The concave-convex portion 62 of the edge 56 on one side and the concave-convex portion 72 of the edge 58 on the other side of the strip-shaped member 42 adjacent along the central axis C of the insertion section 12 both act to maintain the abutted state by the tight contact force caused by the initial tension. Therefore, the concave-convex portion 62 of the edge 56 on one side and the concave-convex portion 72 of the edge 58 on the other side act to maintain a tight contact state between each other. Therefore, it is possible to provide a flexible tube 26 that easily maintains a straight state, and maintains resiliency for returning to the straight state even when being bent. Furthermore, when an external force exceeding an appropriate magnitude is applied to such flexible tube 26, the flexible tube 26 can be bent smoothly.

When bending the flexible tube 26, a compressing force that is larger than the tight contact force caused by the initial tension is applied to a portion that becomes the inner side of the bending radius in the helical tube 32. Therefore, the convex portion 64 of the edge 56 on one side of the strip-shaped member 42 moves towards the concave portion 76 from a position close to the convex portion 74 of the edge 58 on the other side adjacent along the central axis C. Therefore, the portion that becomes the inner side of the bending radius in the helical tube 32 shrinks, and is bent without changing the length of the central axis likewise the outer tube 34. The concave-convex portions 62 and 72 are formed smoothly without any sudden step difference. Therefore, when the flexible tube 26 is bent, it can be bent smoothly.

Furthermore, in the helical tube 32, the initial tension allows the concave-convex portion 62 of the edge 56 on one side and the concave-convex portion 72 of the edge 58 on the other side of the strip-shaped member 42 to be in tight contact with each other in appropriate intervals. In the flexible tube 26, such tight contact force achieves high resiliency (returnability to a linear state). Therefore, since the flexible tube 26 according to the present embodiment returns to the linear state easier than in the case where a tight contact force is not applied between the edge on one side and the edge on the other side of the strip-shaped member 42, the operation of shortening the passage may be easily performed. Since the flexible tube 26 is difficult to deflect, and as easily returned to its original state even if deflected, the force of when an operation is carried out by a user may be easily transmitted to the distal end of the flexible tube 26. Therefore, according to the present embodiment, a flexible tube 26 with favorable insertability can be provided.

Figure 8:
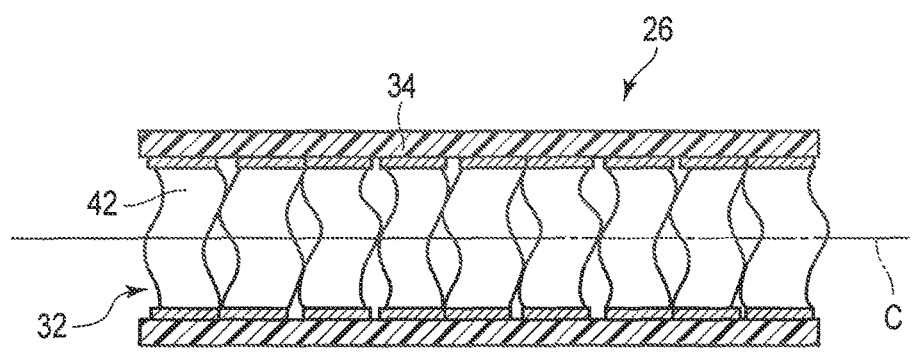
FIG. 8 is a schematic longitudinal sectional view of a state in which an outer tube of the flexible tube of the insertion section of the insertion apparatus is formed in a single layer according to the first embodiment.

In the present embodiment, the outer tube 34 has been explained as being formed in cooperation with the net-like tube 34a and the resin material layer 34b. Additionally, as shown in FIG. 8, the outer tube 34 is also preferable to be formed only by a resin material layer arranged on the outer side of the helical tube 32. In other words, the flexible tube 26 may have a double-layered structure including the helical tube 32 and the resin material layer 34b.

In the present embodiment, although it has been explained that the concave-convex portions 62 and 72 formed on the edges 56 and 58 of the strip-shaped member 42 are in a shape of a sine wave, a variety of shapes may be adopted.

A first modification of the strip-shaped member 42 of the helical tube 32 is shown in FIG. 9A. As shown in FIG. 9A, the concave-convex portions 62 and 72 formed on the edges 56 and 58 of the strip-shaped member 42 may be in a shape of a triangular wave.

As shown in FIG. 9B, in the case where the concave-convex portion 62 of the edge 56 on one side and the concave-convex portion 72 of the edge 58 on the other side among the strip-shaped member 42 adjacent along the central axis C are abutted, the concave-convex portions 62 and 72 are abutted in a line, instead of at a point. Therefore, since a contact area where the concave-convex portions 62 and 72 of the strip-shaped member 42 are in tight contact with each other is large, it is difficult for deviations in the radial direction to occur. In other words, since it is difficult for the strip-shaped member 42 to deviate in the radial direction, it would not interfere with the outer tube 34, allowing the flexible tube to bend smoothly.

A second modification of the strip-shaped member 42 of the helical tube 32 is shown in FIG. 10A. As shown in FIG. 10A, the concave-convex portions 62 and 72 of the edges 56 and 58 of the strip-shaped member 42 may be in a triangular waveform where the apexes are formed as a curved surface.

Figure 10B:
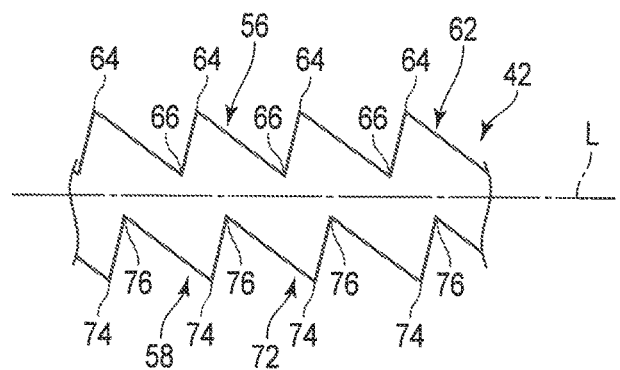
FIG. 10B is a schematic view of a part of a strip-shaped member configuring a helical tube of a flexible tube of an insertion section of an insertion apparatus according to a third modification of the first embodiment.

A third modification of the strip-shaped member 42 of the helical tube 32 is shown in FIG. 10B. As shown in FIG. 10B, the concave-convex portions 62 and 72 of the edges 56 and 58 of the strip-shaped member 42 may be in a shape of a cutting blade.

Figure 10C:
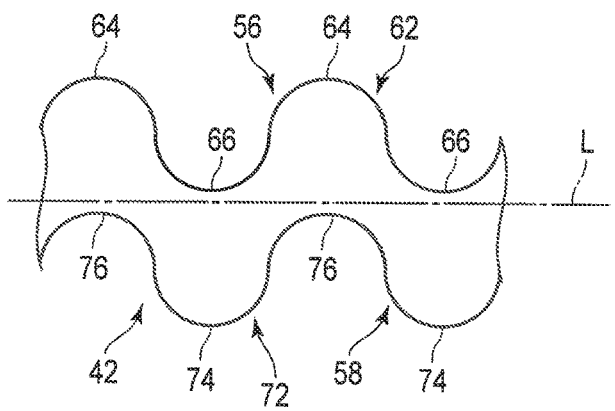
FIG. 10C is a schematic view of a part of a strip-shaped member configuring a helical tube of a flexible tube of an insertion section of an insertion apparatus according to a fourth modification of the first embodiment.

A fourth modification of the strip-shaped member 42 of the helical tube 32 is shown in FIG. 10C. As shown in FIG. 10C, the concave-convex portions 62 and 72 of the edges 56 and 58 of the strip-shaped member 42 may be in a shape obtained by combining circular arcs such as semicircles or elliptic arcs. Although not shown, on the edges 56 and 58 of the strip-shaped member 42 of the helical tube 32, concave-convex portions 62 and 72 may be formed by appropriately combining a part of a plurality of ellipses.

Figure 10D:
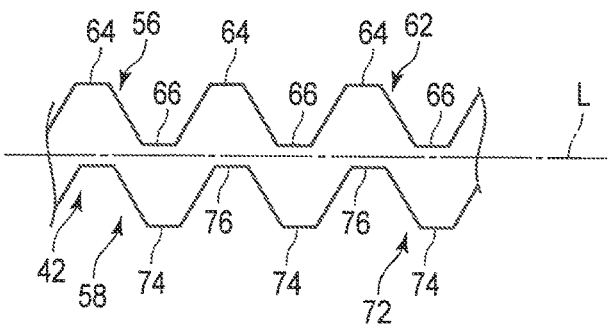
FIG. 10D is a schematic view of a part of a strip-shaped member configuring a helical tube of a flexible tube of an insertion section of an insertion apparatus according to a fifth modification of the first embodiment.

A fifth modification of the strip-shaped member 42 of the helical tube 32 is shown in FIG. 10D. As shown in FIG. 10D, the concave-convex portions 62 and 72 of the edges 56 and 58 of the strip-shaped member 42 may be in a shape obtained by combining trapezoids.

In the above manner, a variety of shapes may be adopted for the concave-convex portions 62 and 72 of the edges 56 and 58 of the strip-shaped member 42 of the helical tube 32. Furthermore, the strip-shaped member 42 may also be formed so that the shapes differ between the edge 56 and the edge 58 on the opposite side of the strip-shaped member 42.

[Second Embodiment]

The second embodiment will be explained using FIG. 11 as follows. The present embodiment is a modification of the first embodiment, in which, to omit detailed explanations, the same symbols as those in the first embodiment will be applied as much as possible to the same members or the members with the same functions as those explained in the first embodiment.

In a flexible tube 26 according to the present embodiment, at an appropriate position between the distal end and the proximal end thereof, a tight contact force caused by the initial tension between strip-shaped member 42 adjacent along the central axis C maintains a constant state in an appropriate range; however, the tight contact force is different for each region of the appropriate range.

When processing the strip-shaped member 42 according to the present embodiment to form a helical tube 32, the tight contact force caused by the initial tension is appropriately changed for each appropriate region along the central axis C. In the present embodiment, the helical tube 32 includes first to third regions (first to third closely-wound regions) $\alpha$, $\beta$, and $\gamma$, in which the tight contact force caused by the initial tension differs between a concave-convex portion 62 of an edge 56 on one side and a concave-convex portion 72 of an edge 58 on the other side of the strip-shaped member 42. In each of the regions $\alpha$, $\beta$, and $\gamma$, it is assumed that the tight contact force between the concave-convex portion 62 of the edge 56 on one side and the concave-convex portion 72 of the edge 58 on the other side of the strip-shaped member 42 is substantially constant, respectively.

In the present embodiment, it is assumed that the first region $\alpha$ includes the distal end part of the helical tube 32, and the third region $\gamma$ includes the proximal end part of the helical tube 32. In the first region $\alpha$ of the helical tube 32, compared to the second and third regions $\beta$ and $\gamma$, the tight contact force between the concave-convex portion 62 of the edge 56 on one side and the concave-convex portion 72 of the edge 58 on the other side of the strip-shaped member 42 is smaller. In the second region $\beta$ of the helical tube 32, the tight contact force between the concave-convex portion 62 of the edge 56 on one side and the concave-convex portion 72 of the edge 58 on the other side is larger than the first region $\alpha$, and smaller than third region $\gamma$. In other words, in the third region $\gamma$ of the helical tube 32, compared to the first and second regions $\alpha$ and $\beta$, the tight contact force between the concave-convex portion 62 of the edge 56 on one side and the concave-convex portion 72 of the edge 58 on the other side of the strip-shaped member 42 is larger.

A frictional force between the concave-convex portions 62 and 72 of the strip-shaped member 42 increases in proportion to the tight contact force. In the first region $\alpha$, the tight contact force between the concave-convex portion 62 of the edge 56 on one side and the concave-convex portion 72 of the edge 58 on the other side of the strip-shaped member 42 is smaller than each of the tight contact force of the second and third regions $\beta$ and $\gamma$. Therefore, in the first region $\alpha$, the frictional force between the concave-convex portion 62 of the edge 56 on one side and the concave-convex portion 72 of the edge 58 on the other side of the strip-shaped member 42 is smaller than each of the frictional force of the second and third regions $\beta$ and $\gamma$. Therefore, in the first region $\alpha$, compared to the second and third regions $\beta$ and $\gamma$, the concave-convex portions 62 and 72 are more easily isolated from each other and easily positionally deviated.

In the same manner, in the second region $\beta$, compared to the third region $\gamma$, the concave-convex portions 62 and 72 are more easily isolated from each other and easily positionally deviated. In the third region $\gamma$, compared to the first and second regions $\alpha$ and $\beta$, it is difficult for the concave-convex portions 62 and 72 to be isolated from each other and it is difficult for them to be positionally deviated. Therefore, regarding the flexible tube 26, a portion corresponding to the first region $\alpha$ of the helical tube 32 is bent easier than a portion corresponding to the second region $\beta$ of the helical tube 32. A portion corresponding to the second region $\beta$ of the helical tube 32 is more easily bent than a portion corresponding to the third region $\gamma$ of the helical tube 32. Therefore, regarding the flexible tube 26, the portion corresponding to the first region $\alpha$ of the helical tube 32 is more easily bent than portions corresponding to the second region $\beta$ and the third region $\gamma$. In other words, in the third region $\gamma$, a bending tolerance of the flexible tube 26 becomes the highest.

On the other hand, regarding the flexible tube 26, the initial tension (tight contact force) of the portion corresponding to the third region $\gamma$ of the helical tube 32 is larger than each of the initial tension of the portions corresponding to the first and second regions $\alpha$ and $\beta$ of the helical tube 32. Therefore, regarding the flexible tube 26, the portion corresponding to the third region $\gamma$ of the helical tube 32 returns more easily to an original state from a bent state than the portions corresponding to the first and second regions $\alpha$ and $\beta$. In other words, while appropriate resiliency is maintained in the first to third regions $\alpha$, $\beta$, and $\gamma$, the resiliency of the third region $\gamma$ becomes larger than each of the resiliency of the first and second regions $\alpha$ and $\beta$, and the resiliency of the second region $\beta$ becomes larger than the resiliency of the first region $\alpha$.

Furthermore, the tight contact force caused by the initial tension is applied to both the boarder between the first region $\alpha$ and the second region $\beta$, and the boarder between the second region $\beta$ and the third region $\gamma$. Therefore, the helical tube 32 is suppressed from drastic changes in the resiliency and drastic changes in the unbendability at these borders.

In contrast, when the initial tension is reduced between the concave-convex portions 62 and 72 adjacent along the central axis C, the frictional force decreases at a portion where the concave-convex portions 62 and 72 of the strip-shaped member 42 come in contact with each other. Therefore, the concave-convex portions 62 and 72 of the strip-shaped member 42 become easily positionally deviated, and the flexible tube 26 becomes flexible in bending. In the above manner, by changing the initial tension of the helical tube 32 in the axial direction, it is possible to change the hardness of bending the flexible tube 26 in the axial direction.

As explained above, the flexible tube 26 according to the present embodiment is capable of voluntarily changing the hardness of bending the flexible tube in the axial direction while maintaining a state that has resiliency with favorable insertability. Since the flexible tube 26 becomes harder towards the proximal side from the distal side, by making the distal side of the flexible tube 26 flexible so that, for example, it bends along the shape of the large intestine, and by making the proximal side harder so that a force is easily transmitted to the distal end part, the insertability of the flexible tube 26 can be further improved. Furthermore, by changing the tight contact force of the helical tube 32 caused by the initial tension along the axial direction of the central axis C, the hardness of the flexible tube 26 can be changed independently of the outer tube 34. In each region, by applying the tight contact force caused by the appropriate initial tension, the flexible tube 26 can be adjusted to a desired unbendability along the axial direction of the central axis C thereof.

[Third Embodiment]

The third embodiment will be explained using FIG. 12 in the following. The present embodiment is a modification of the first and second embodiments, in which, to omit detailed explanations, the same symbols as those in the first and second embodiments will be applied whenever possible to the same members or the members with the same functions as those explained in the first and second embodiments.

As shown in FIG. 12, on at least a surface where the concave-convex portions 62 and 72 of the adjacent strip-shaped member 42 come in contact with each other in the strip-shaped member 42 configuring the helical tube 32a, a processing to change the friction coefficient is applied. Here, to simplify the explanation, as explained in the first embodiment, the initial tension to be added between the concave-convex portion 62 of the edge 56 on one side and the concave-convex portion 72 of the edge 58 on the other side of the strip-shaped member 42 is assumed as being constant. Furthermore, the friction coefficient is changed in each of the first region α, the second region β, and the third region γ explained in the second embodiment, that is, the first to third closely-wound regions.

In the present embodiment, as explained in the second embodiment, an example of making the flexible tube 26 more flexible towards the region on the distal side for easy bendability will be explained.

In the first region α of the helical tube 32, the edge 56 on one side indicated by a dashed line and the edge 58 on the other side indicated by a dashed line of the strip-shaped member 42 are smoothly formed. In the first region α, the edge 56 on one side and the edge 58 on the other side of the strip-shaped member 42 are coated with, for example, a PTFE material. In the helical tube 32, the frictional force between the concave-convex portion 62 of the edge 56 on one side and the concave-convex portion 72 of the edge 58 on the other side is made lower than a state in which a coating is not applied to the edges 56 and 58 of the strip-shaped member 42.

In the second region β of the helical tube 32, the edge 56 on one side indicated by a dashed line and the edge 58 on the other side indicated by a solid line of the strip-shaped member 42 are smoothly formed. In the second region β, the edge 56 on one side of the strip-shaped member 42 indicated by a dashed line, that is, at least a part of the edge 56, is coated with, for example, a PTFE material. In the second region β, the edge 58 on the other side of the strip-shaped member 42 indicated by a solid line is not coated.

In the third region γ of the helical tube 32, the edge 56 on one side and the edge 58 on the other side of the strip-shaped member 42 are formed smoothly in the same manner as the first and second regions α and β. In the third region γ, the edge 56 on one side and the edge 58 on the other side of the strip-shaped member 42 are not coated.

In the first region α, the friction coefficient is changed to be reduced by applying a coating to each of both surfaces at which the concave-convex portions 62 and 72 of the strip-shaped member 42 adjacent along the central axis C come in contact with each other. Therefore, in the first region α, the concave-convex portions 62 and 72 of the strip-shaped member 42 adjacent along the central axis C are made to be easily deviated. Therefore, in the flexible tube 26, a portion corresponding to the first region α of the helical tube 32 is easier to bend than a portion where the processing is not applied.

In the second region β, the friction coefficient is changed to be reduced by applying a coating to one of the surfaces at which the concave-convex portions 62 and 72 of the strip-shaped member 42 adjacent along the central axis C come in contact with each other. Therefore, in the second region β, although not as easily deviated as in the first region α, the concave-convex portions 62 and 72 of the strip-shaped member 42 adjacent along the central axis C are easily deviated. Therefore, in the flexible tube 26, the portion corresponding to the second region β of the helical tube 32 is not easier to bend than the portion corresponding to the first region α, however, is easier to bend than the portion to which the processing is not applied (the portion corresponding to the third region γ).

Therefore, by using the flexible tube 26 including the helical tube 32 that is wound while applying the tight contact force caused by the initial tension in a state where the friction coefficient of a part of the concave-convex portions 62 and 72 of the edges 56 and 58 of the strip-shaped member 42 is appropriately changed, while maintaining the hardness of the flexible tube 26 against bending in a constant state in each of the regions α, β, and γ, this may be appropriately changed for other regions.

Furthermore, regarding the returnability (resiliency) of the flexible tube 26 from a bent state, the resiliency is made the highest in the first region α where the friction coefficient is the smallest, and the resiliency is made high in the second region β where the friction coefficient is smaller. Therefore, while maintaining the returnability of the flexible tube 26 from the bent state to the linear state in a constant state in each of the regions α, β, and γ, the returnability can be changed as appropriate for the other regions.

For the above matters, an opposite relationship is established regarding the processing for increasing the friction coefficient. For example, in the first region α, a processing for changing the friction coefficient is not applied to the concave-convex portions 62 and 72 that come in contact with each other by the tight contact force. In the second region β, the concave-convex portions 62 and 72 that come in contact with each other by the tight contact force are such that the processing for increasing the friction coefficient, such as a roughening processing, is applied to the concave-convex portion 62 of the edge 56 on one side, and the processing for changing the friction coefficient is not applied to the concave-convex portion 72 of the edge 58 on the other side. In the third region γ, as a processing for changing the friction coefficient, for example, a roughening processing is applied to the concave-convex portions 62 and 72 that come in contact with each other by the tight contact force.

If the friction coefficient between the concave-convex portion 62 of the edge 56 on one side and the concave-convex portion 72 of the edge 58 on the other side is increased, it would be difficult for the concave-convex portions 62 and 72 to slide against each other in the circumferential direction. Therefore, at portions receiving the processing to increase the friction coefficient of the concave-convex portions 62 and 72 that come in contact with each other by the tight contact force, the flexible tube 26 becomes difficult to bend.

In addition, for example, the PTFE coating may be applied to at least one of the edge 56 on one side and the edge 58 on the other side of the first region α, and the roughening processing may be applied to at least one of the edge 56 on one side and the edge 58 on the other side of the third region γ.

The roughening processing is capable of making the frictional forces different between the frictional force of when bending the flexible tube 26 from a straight state and deviating the positions of the first and second concave-convex portions 62 and 72 from the original positions along the longitudinal axis L, and the frictional force of when returning the flexible tube 26 to the straight state from the bent state and returning the positions of the first and second concave-convex portions 62 and 72 to the original position. For example, a roughening processing can be performed to make bending difficult when bending the flexible tube 26 that is in a straight state, and to make returning easier when returning the flexible tube 26 that is in a bent state to a straight state. It is also possible to perform the opposite depending on the processing. Therefore, the roughening processing can be designed to have directionality.

The insertion apparatus 10 according to the present embodiment is capable of exercising the following effects.

The hardness for bending the flexible tube 26 in the axial direction can be changed voluntarily while maintaining resiliency with favorable insertability by appropriately changing the friction coefficients between the concave-convex portions 62 and 72 of the edges 56 and 58 of the strip-shaped member 42 of the helical tube 32. For example, the distal side of the flexible tube 26 can be made flexible so as to be bent along the shape of, for example, the large intestine (bent by the external force received from a body wall, such as the large intestine), and the proximal side can be made hard so as to easily transmit the force to the distal end part of the insertion section 12. Therefore, the insertability of the flexible tube 26 can be further improved. Furthermore, by changing the friction coefficient of the surface on which the concave-convex portions 62 and 72 of the adjacent strip-shaped member 42 come in contact, the hardness of the flexible tube 26 can be changed independent of the outer tube 34, thereby, allowing the flexible tube 26 to have a desired hardness.

As mentioned above, by changing the friction coefficients as appropriate, such as by coating or roughening the edges 56 and 58 of each region α, β, and γ of the helical tube 32, the bendability/unbendability of the flexible tube 26, and easiness/difficulty to return to the straight state can be set to a desired state.

In the helical tube 32 of the flexible tube 26 according to the present embodiment, the tight contact force caused by the initial tension does not have to be changed between the concave-convex portions 62 and 72 of the edges 56 and 58 of the strip-shaped member 42 as explained in the second embodiment. The helical tube 32 of the flexible tube 26 according to the present embodiment is capable of changing the hardness against bending of the flexible tube 26 in a state where the tight contact force caused by the initial tension is maintained constant. Therefore, the distal side of the flexible tube 26 according to the present embodiment can be made flexible while maintaining resiliency with favorable insertability. Therefore, a flexible tube 26 with a more favorable insertability than the flexible tube 26 explained in the second embodiment can be provided.

By using the processing for reducing and the processing for increasing the friction coefficient appropriately for the portions where the concave-convex portions 62 and 72 of the edges 56 and 58 of the strip-shaped member 42 of the helical tube 32 come in contact with each other, the hardness against bending of the flexible tube 26 can be changed stepwise. By changing the friction coefficient of the contact part of the concave-convex portions 62 and 72 of the strip-shaped member 42 adjacent in the above manner to an axial direction, the hardness of the flexible tube 26 can be changed to the axial direction.

In the case where the friction coefficient is to be increased, in addition to carrying out the roughening processing on the portions where the concave-convex portions 62 and 72 of the edges 56 and 58 of the strip-shaped member 42 come in contact with each other, the roughening processing may be performed by applying chemical processing, etc. or spraying glass beads, etc.

Here, a case in which the initial tension applied between the concave-convex portion 62 of the edge 56 on one side and the concave-convex portion 72 of the edge 58 on the other side of the strip-shaped member 42 is made constant, is explained. As explained in the second embodiment, the tight contact force caused by the initial tension may, of course, be changed between the concave-convex portion 62 of the edge 56 on one side and the concave-convex portion 72 of the edge 58 on the other side of the strip-shaped member 42 in each region. That is, needless to say, the friction coefficients of the concave-convex portion 62 of the edge 56 on one side and the concave-convex portion 72 of the edge 58 on the other side of the strip-shaped member 42 may be set as appropriate, and the tight contact force caused by the initial tension may be changed between the concave-convex portion 62 of the edge 56 on one side and the concave-convex portion 72 of the edge 58 on the other side of the strip-shaped member 42.

[Fourth Embodiment]

Figure 14A:
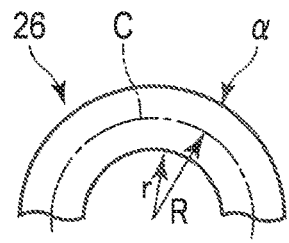
FIG. 14A is a schematic view of a minimum bending radius of the flexible tube including the first region of the insertion section of the insertion apparatus according to the fourth embodiment.
Figure 14B:
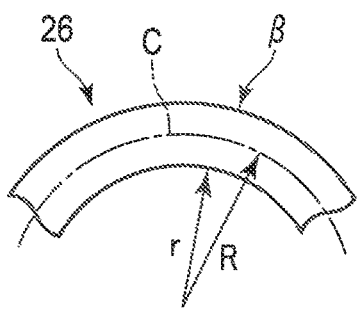
FIG. 14B is a schematic view of a state in which the flexible tube including the second region has a larger minimum bending radius than a portion including the first region.
Figure 14C:
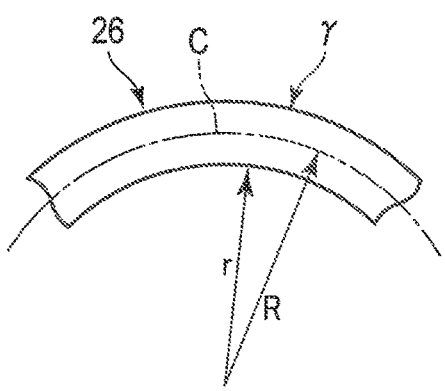
FIG. 14C is a schematic view of a state in which the flexible tube including the third region has a larger minimum bending radius than portions including the first and the second regions.

The fourth embodiment will be explained using FIG. 13 to FIG. 14C in the following. The present embodiment is a modification of the first to third embodiments, in which, to omit detailed explanations, the same symbols as those in the first to third embodiments will be applied whenever possible to the same members or the members with the same functions as those explained in the first to third embodiments.

An example of adjusting a minimum bending radius R that coincides with a central axis C at a position along the central axis C of a flexible tube 26 will be explained. Here, the bending radius that coincides with the central axis C when the flexible tube 26 cannot be bent further is referred to as the minimum bending radius R.

As explained in the first embodiment, the initial tension between the concave-convex portion 62 of the edge 56 on one side and the concave-convex portion 72 of the edge 58 on the other side of the strip-shaped member 42 is made constant, and, as shown in FIG. 13, the first region α, the second region β, and the third region γ, i.e. the first to third closely-wound regions explained in the second embodiment are defined.

In the present embodiment, the concave-convex portion 62 of the edge 56 on one side and the concave-convex portion 72 of the edge 58 on the other side of the strip-shaped member 42 are not uniform along the longitudinal axis L, and are different for each region. As shown in FIG. 13, in the first region α, the difference between the apex of the convex portion 64 and the most concaved position of the concave portion 66 of the concave-convex portion 62 of the edge 56 on one side, and the difference between the apex of the convex portion 74 and the most concaved position of the concave portion 76 of the concave-convex portion 72 of the edge 58 on the other side are referred to as Ha. In the second region β, the difference between the apex of the convex portion 64 and the most concaved position of the concave portion 66 of the concave-convex portion 62 of the edge 56 on one side, and the difference between the apex of the convex portion 74 and the most concaved position of the concave portion 76 of the concave-convex portion 72 of the edge 58 on the other side are referred to as Hb. In the third region γ, the difference between the apex of the convex portion 64 and the most concaved position of the concave portion 66 of the concave-convex portion 62 of the edge 56 on one side, and the difference between the apex of the convex portion 74 and the most concaved position of the concave portion 76 of the concave-convex portion 72 of the edge 58 on the other side are referred to as Hc.

In each region of α, β, and γ, the difference between the apex of the convex portion 64 and the most concaved position of the concave portion 66 of the concave-convex portion 62 of the edge 56 on one side, and the difference between the apex of the convex portion 74 and the most concaved position of the concave portion 76 of the concave-convex portion 72 of the edge 58 on the other side are assumed as being respectively constant.

In the present embodiment, the difference Ha in the first region α is larger than the difference Hb in the second region β. The difference Hb in the second region β is larger than the difference Hc in the third region γ.

Therefore, greater movement is possible for the portion between the concave-convex portion 62 of the edge 56 on one side and the concave-convex portion 72 of the edge 58 on the other side of the strip-shaped member 42 in the first region α than each of the portion of the second and third regions β and γ. Greater movement is possible for the portion between the concave-convex portion 62 of the edge 56 on one side and the concave-convex portion 72 of the edge 58 on the other side of the strip-shaped member 42 in the second region β than each of the portion of the third region γ. Accordingly, the minimum bending radius R that coincides with the central axis C in the first region α shown in FIG. 14A can be made smaller than the minimum bending radius R of the second region β shown in FIG. 14B and the minimum bending radius R of the third region γ shown in FIG. 14C. The minimum bending radius R that coincides with the central axis C in the second region β shown in FIG. 14B can be made smaller than the minimum bending radius R that coincides with the central axis C in the third region γ shown in FIG. 14C.

For example, when a portion corresponding to the first region α is bent in the flexible tube 26, on the inner circumference side of the bending radius of the helical tube 32, the convex portion 64 of the edge 56 on one side of the strip-shaped member 42 moves relatively towards the concave portion 76 from the convex portion 74 of the edge 58 on the other side. On the outer circumference side of the bending radius of the helical tube 32, the concave-convex portion 62 of the edge 56 on one side of the strip-shaped member 42 becomes separated from the concave-convex portion 72 of the edge 58 on the other side. The flexible tube 26 can be bent by moving each of the strip-shaped member 42 of the helical tube 32.

Furthermore, when a portion corresponding to, for example, the first region α is bent in the flexible tube 26, the vicinity of the apex of the convex portion 64 of the edge 56 on one side of the strip-shaped member 42 comes in contact in the vicinity of the most concaved portion of the concave portion 76 of the edge 58 on the other side. When the vicinity of the apex of the convex portion 64 of the edge 56 on one side of the strip-shaped member 42 comes in contact in the vicinity of the most concaved portion of the concave portion 76 of the edge 58 on the other side, the inner circumference side of the helical tube 32 would not be able to shrink further. Therefore, the minimum bending radius R of the portion corresponding to, for example, the first region α in the flexible tube 26 is determined.

In a similar manner, the minimum bending radius R of the portion corresponding to the second region β and the minimum bending radius R of the portion corresponding to the third region γ in the flexible tube 26 are respectively determined.

Here, by providing the difference Ha in the first region α, the difference Hb in the second region β, and the difference Hc in the third region γ (Ha>Hb>Hc), the minimum bending radius R along the central axis C of the flexible tube 26 can be changed appropriately. That is, as shown in FIG. 13, by changing the differences (amplitude differences) Ha, Hb, and Hc of the concave-convex portions 62 and 72 of the strip-shaped member 42 along the central axis C of the helical tube 32, the length in which the inner circumference side of the helical tube 32 shrinks until the convex portion 64 of the edge 56 on one side and the concave portion 76 of the edge 58 on the other side of the strip-shaped member 42 come in contact can be changed. By changing the minimum bending radius R that coincides with the central axis C, a minimum inner side bending radius r in each of the regions α, β, and γ (refer to FIG. 14A to FIG. 14C) can be changed.

As explained above, according to the insertion apparatus 10 of the present embodiment, the following effects may be obtained.

The flexible tube 26 according to the present embodiment is capable of voluntarily changing the minimum bending radius R for the bending of the flexible tube 26 in the axial direction while maintaining a state having resiliency with favorable insertability.

In order to allow bending in a smaller radius along, for example, the shape of the large intestine, for example, the minimum bending radius R of the distal end part of the flexible tube 26 can be made smaller than the other portions (proximal side). By making the minimum bending radius R of the proximal end part of the flexible tube 26 larger than the distal side, the amount of deflection can be suppressed compared to the distal end part even if the proximal end part of the flexible tube 26 is bent. Therefore, the insertability of when inserting the distal end of the insertion section 12 (flexible tube 26) into a hole can be improved with respect to the distal end of the flexible tube.

In the present embodiment, the difference Ha between the apex of the convex portion 64 and the most concaved position of the concave portion 66 of the concave-convex portion 62 of the edge 56 on one side in the first region α of the helical tube 32 has been assumed as being uniform in the first region α. However, it is also favorable to make the differences gradually smaller from the distal side towards the proximal side. This also applies to the second region β and the third region γ. That is, it is also favorable to make the difference between the apex of the convex portion 64 and the most concaved position of the concave portion 66 of the concave-convex portion 62 of the edge 56 on one side of the helical tube 32, and the difference between the apex of the convex portion 74 and the most concaved position of the concave portion 76 of the concave-convex portion 72 of the edge 58 on the other side, gradually smaller from the distal side towards the proximal side of the helical tube 32.

[Fifth Embodiment]

The fifth embodiment will be explained using FIG. 15 to FIG. 16C in the following. The present embodiment is a modification of the first to fourth embodiments, in which, to omit detailed explanations, the same symbols as those in the first to fourth embodiments will be applied whenever possible to the same members or the members with the same functions as those explained in the first to fourth embodiments.

Here, an example of adjusting the minimum bending radius R that coincides with the central axis C by a position along the central axis C of the flexible tube 26 with a structure that is different from the fourth embodiment will be explained.

Figure 15:
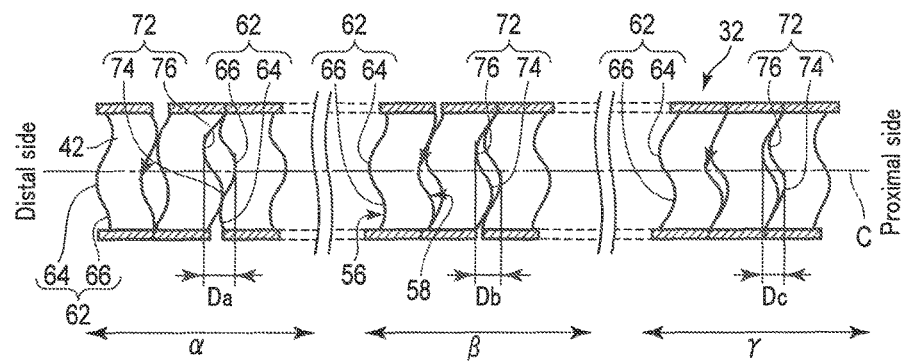
FIG. 15 is a schematic longitudinal sectional view of a first region, a second region, and a third region of a helical tube of a flexible tube of an insertion section of an insertion apparatus according to a fifth embodiment, showing a state in which a distance between a most concaved position of a concave portion of a concave-convex portion of an edge on one side and a most concaved position of a concave portion of a concave-convex portion of an edge on the other side of a strip-shaped member adjacent along a central axis is changed in each region.
Figure 16A:
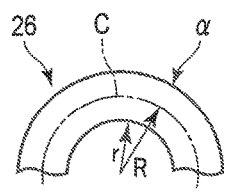
FIG. 16A is a schematic view of a minimum bending radius of the flexible tube including the first region of the insertion section of the insertion apparatus according to the fifth embodiment.
Figure 16B:
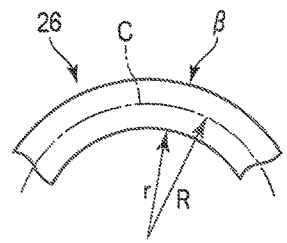
FIG. 16B is a schematic view of a state in which the flexible tube including the second region has a larger minimum bending radius than a portion including the first region.
Figure 16C:
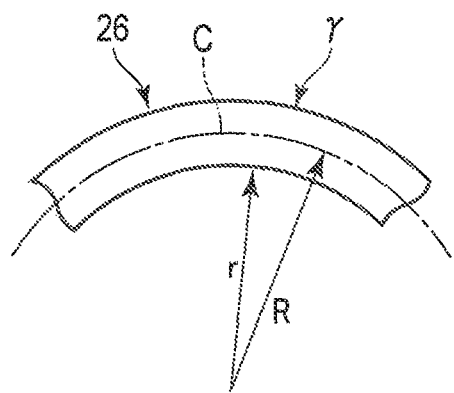
FIG. 16C is a schematic view of a state in which the flexible tube including the third region has a larger minimum bending radius than portions including the first and the second regions.

As explained in the first embodiment, the initial tension applied between the concave-convex portion 62 of the edge 56 on one side and the concave-convex portion 72 of the edge 58 on the other side of the strip-shaped member 42 will be made constant in each of the regions α, β, and γ, and, as shown in FIG. 15, the first region α, the second region β, and the third region γ (first to third closely-wound regions) explained in the second embodiment will be defined.

In the present embodiment, the concave-convex portion 62 of the edge 56 on one side and the concave-convex portion 72 of the edge 58 on the other side of the strip-shaped member 42 are not uniform along the longitudinal axis L, and are different for each region. As shown in FIG. 15, a distance between the most concaved position of the concave portion 66 of the concave-convex portion 62 of the edge 56 on one side and the most concaved position of the concave portion 76 of the concave-convex portion 72 of the edge 58 on the other side in the first region α will be referred to as Da. A distance between the most concaved position of the concave portion 66 of the convex portion 64 of the concave-convex portion 62 of the edge 56 on one side and the most concaved position of the concave portion 76 of the concave-convex portion 72 of the edge 58 on the other side in the second region β will be referred to as Db. A distance between the most concaved position of the concave portion 66 of the convex portion 64 of the concave-convex portion 62 of the edge 56 on one side and the most concaved position of the concave portion 76 of the concave-convex portion 72 of the edge 58 on the other side in the third region γ will be referred to as Dc.

In each region of α, β, and γ, the distance between the most concaved position of the concave portion 66 of the concave-convex portion 62 of the edge 56 on one side, and the most concaved position of the concave portion 76 of the concave-convex portion 72 of the edge 58 on the other side is assumed as being respectively constant.

As shown in FIG. 15, a relative position at which the concave-convex portions 62 and 72 of the strip-shaped member 42 are in tight contact is changed along the central axis C of the flexible tube 26. In the first region α, the apex of the convex portion 64 of the concave-convex portion 62 of the edge 56 on one side is in tight contact in the vicinity of the apex of the convex portion 74 of the concave-convex portion 72 of the edge 58 on the other side adjacent along the central axis C. In the second region β, the apex of the convex portion 64 of the concave-convex portion 62 of the edge 56 on one side is in tight contact at a position (for example, a boundary position between the convex portion 74 and the concave portion 76) between the convex portion 74 and the concave portion 76 of the concave-convex portion 72 of the edge 58 on the other side adjacent along the central axis C. In the third region γ, the apex of the convex portion 64 of the concave-convex portion 62 of the edge 56 on one side is in tight contact at a position in the vicinity of the most concaved position of the concave portion 76 of the concave-convex portion 72 of the edge 58 on the other side adjacent along the central axis C.

In the present embodiment, the distance Da in the first region α is longer than the distance Db in the second region β. The distance Db in the second region β is longer than the distance Dc in the third region γ.

Therefore, greater movement is possible for the portion between the concave-convex portion 62 of the edge 56 on one side and the concave-convex portion 72 of the edge 58 on the other side of the strip-shaped member 42 in the first region α than each of the portion of the second and third regions β and γ. Greater movement is possible for the portion between the concave-convex portion 62 of the edge 56 on one side and the concave-convex portion 72 of the edge 58 on the other side of the strip-shaped member 42 in the second region β than the portion of the third region γ. Therefore, the minimum bending radius R that coincides with the central axis C in the first region α shown in FIG. 16A can be made smaller than the minimum bending radius R of the second region β shown in FIG. 16B and the minimum bending radius R of the third region γ shown in FIG. 16C. The minimum bending radius R that coincides with the central axis C in the second region β can be made smaller than the minimum bending radius R that coincides with the central axis C in the third region γ.

As shown in FIG. 15, by changing the tight contact position of the concave-convex portions 62 and 72 of the strip-shaped member 42, the length is changed in which the inner circumference side of the bending radius of the helical tube 32 shrinks until the convex portion 64 of the edge 56 on one side of the strip-shaped member 42 and the concave portion 76 of the edge 58 on the other side adjacent along the central axis C come in contact.

The above tight contact position of the concave-convex portions 62 and 72 of the strip-shaped member 42 can be changed by changing, for example, the length (frequency) of each of the convex portions 64 and 74 and the concave portions 66 and 76 along the longitudinal axis L of the concave-convex portions 62 and 72. In the flexible tube 26, in the case of making the minimum bending radius R of the distal end part small, the length of each of the convex portions 64 and 74 and the concave portions 66 and 76 along the longitudinal axis L of the concave-convex portions 62 and 72 is made longer; and, in the case of making the minimum bending radius R of the proximal end part larger, the length of each of the convex portions 64 and 74 and the concave portions 66 and 76 along the longitudinal axis L of the concave-convex portions 62 and 72 is made shorter. By changing the minimum bending radius R that coincides with the central axis C, a minimum inner circumference side bending radius r in each of the regions α, β, and γ (refer to FIG. 16A to FIG. 16C) can be changed.

As explained above, according to the insertion apparatus 10 related to the present embodiment, the following effects may be obtained.

The flexible tube 26 according to the present embodiment is capable of voluntarily changing the minimum bending radius R for the bending of the flexible tube 26 in the axial direction while maintaining a state having resiliency with favorable insertability.

In order to allow bending in a smaller radius along, for example, the shape of the large intestine, the minimum bending radius R of, for example, the distal end part of the flexible tube 26 can be made smaller than the other portions (proximal side). By making the minimum bending radius R of the proximal end part of the flexible tube 26 larger than the distal side, the amount of deflection can be controlled compared to the distal end part, even if the proximal end part of the flexible tube 26 is bent. Therefore, the insertability when inserting the distal end of the insertion section 12 (flexible tube 26) into a hole can be improved with respect to the distal end of the flexible tube.

In the present embodiment, although the distance Da between the most concaved position of the concave portion 66 of the concave-convex portion 62 of the edge 56 on one side and the most concaved position of the concave portion 76 of the concave-convex portion 72 of the edge 58 on the other side in the first region α is assumed as being uniform in the first region α, it is also favorable to gradually reduce the difference from the distal side towards the proximal side. This also applies to the second region β and the third region γ. That is, it is also favorable to gradually reduce the distance between the most concaved position of the concave portion 66 of the concave-convex portion 62 of the edge 56 on one side and the most concaved position of the concave portion 76 of the concave-convex portion 72 of the edge 58 on the other side of the strip-shaped member 42 from the distal side towards the proximal side of the helical tube 32.

In the above-mentioned embodiment, the endoscope in FIG. 1 has been shown and explained as the insertion apparatus 10; however, instead of using the insertion section 12, for example, the above-mentioned flexible tube 26 may also be used for a catheter, etc. that is not shown.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube used as a part of an insertion section which defines a central axis of an insertion apparatus to be inserted into a hole, the flexible tube comprising:
  a helical tube comprising a closely-wound region, the helical tube being formed of a strip-shaped member that is spirally wound around the central axis, the strip-shaped member comprising:
    a first edge and a second edge, each extending along a length of the strip-shaped member, and
    a concave-convex portion which is provided on each of the first edge and the second edge of the strip-shaped member, and which alternately includes convex portions and concave portions; and
  a cylindrical outer tube which covers an outer surface of the helical tube, wherein:
  the helical tube is bendable;
  each of the convex portions of the concave-convex portion comprises an apex;
  the convex portions of the concave-convex portion at the first edge and the convex portions of the concave-convex portion at the second edge that face each other along the central axis in the closely-wound region of the helical tube are compressed to each other at least when the helical tube is in a straight state; and
  regardless of whether the helical tube is in the straight state or in a bent state, at least one convex portion at the first edge that faces a respective convex portion at the second edge along the central axis is in tight contact with the respective convex portion at the second edge at a position off the apex of the at least one convex portion at the first edge and a position off the apex of the respective convex portion at the second edge.

2. The flexible tube according to claim 1, wherein the helical tube is configured in the closely-wound region across an entire length thereof along the central axis.

3. The flexible tube according to claim 1, wherein the concave-convex portion is in a shape including at least one of a sine wave, a triangular wave, a circular arc, and an elliptic arc.

4. The flexible tube according to claim 1, wherein the helical tube has resiliency which allows the concave-convex portions facing each other along the central axis to move with respect to each other in response to a bending amount of the flexible tube while maintaining a contact state between:
  a convex portion at the first edge, and
  a convex portion and/or a concave portion at the second edge.

5. The flexible tube according to claim 1, wherein the closely-wound region of the helical tube comprises a first region in which convex portions at the first edge and convex portions at the second edge are compressed to each other along the central axis by a first compressing force, and a second region in which convex portions at the first edge and convex portions at the second edge are compressed to each other along the central axis by a second compressing force that is higher than the first compressing force.

6. The flexible tube according to claim 1, wherein, on at least a part of the closely-wound region of the helical tube, a processing to change a friction coefficient at a portion where the concave-convex portions facing each other along the central axis come in contact has been performed.

7. The flexible tube according to claim 1, wherein
  the closely-wound region of the helical tube comprises a first region and a second region; and
  a height of a convex portion from a point corresponding to a most concaved position of an adjacent concave portion to the apex of the convex portion in the second region is smaller than a height of a convex portion in the first region.

8. The flexible tube according to claim 1, wherein
  the closely-wound region of the helical tube comprises a first region and a second region; and
  a distance between a most concaved position of the concave portion of the concave-convex portion at the first edge and a most concaved position of the concave portion of the concave-convex portion at the second edge in the second region is smaller than a distance between a most concaved position of a concave portion of the concave-convex portion at the first edge and a most concaved position of a concave portion of the concave-convex portion at the second edge in the first region.

9. The flexible tube according to claim 1, wherein the outer tube comprises a net-like tube arranged on an outer side of the helical tube, and a resin material layer covering an outer side of the net-like tube.

10. The flexible tube according to claim 1, wherein, when the helical tube is in the straight state, each of the convex portions at the first edge that faces a respective convex portion at the second edge along the central axis in the closely-wound region is in tight contact with the respective convex portion at the second edge at a position deviated from the apex of each of the convex portions at the first edge and a position deviated from the apex of the respective convex portion at the second edge.

11. An insertion apparatus comprising an insertion section which is insertable into a hole, comprising the flexible tube according to claim 1.

12. A flexible tube used as a part of an insertion section which defines a central axis of an insertion apparatus to be inserted into a hole, the flexible tube comprising:
  a helical tube comprising a closely-wound region, the helical tube being formed of a strip-shaped member that is spirally wound around the central axis, the strip-shaped member comprising:
    a first edge and a second edge, each extending along a length of the strip-shaped member, and
    a concave-convex portion which is provided on each of the first edge and the second edge, and which alternately includes convex portions and concave portions; and
  a cylindrical outer tube which covers an outer surface of the helical tube,
  wherein
    the helical tube is bendable;
    each of the convex portions of the concave-convex portion comprises an apex;
    the convex portions of the concave-convex portion at the first edge and the convex portions of the concave-convex portion at the second edge that face each other along the central axis in the closely-wound region of the helical tube are compressed to each other at least when the helical tube is in a straight state; and the helical tube has resiliency which allows the concave-convex portions facing each other along the central axis to move with respect to each another in a direction of the length of the strip-shaped member in response to a bending amount of the flexible tube while maintaining a contact state between:
- at least one convex portion at the first edge, and
- a convex portion and/or a concave portion at the second edge.

13. The flexible tube according to claim 12, wherein, when the helical tube is subjected to a bending force, the concave-convex portions facing each other along the central axis are configured to move with respect to each other such that at least one convex portion at the first edge moves from a position in contact with a vicinity of the apex of a convex portion at the second edge towards a position in contact with a concave portion at the second edge, while maintaining a state of contact between:
- the at least one convex portion at the first edge, and
- the convex portion and/or the concave portion at the second edge.

14. An insertion apparatus comprising an insertion section which is insertable into a hole, comprising the flexible tube according to claim 12.

* * * * *